(12) United States Patent
Sakamoto et al.

(10) Patent No.: US 10,077,297 B2
(45) Date of Patent: Sep. 18, 2018

(54) FC FUSION HIGH AFFINITY IGE RECEPTOR α-CHAIN

(71) Applicant: Kissei Pharmaceutical Co., Ltd., Matsumoto-shi, Nagano (JP)

(72) Inventors: Takashi Sakamoto, Azumino (JP); Yoichi Inada, Azumino (JP); Kazumasa Yokoyama, Azumino (JP)

(73) Assignee: Kissei Pharmaceutical Co., Ltd., Matsumoto-shi, Nagano (JP)

( * ) Notice: Subject to any disclaimer, the term of this patent is extended or adjusted under 35 U.S.C. 154(b) by 0 days.

(21) Appl. No.: 15/552,065

(22) PCT Filed: Feb. 19, 2016

(86) PCT No.: PCT/JP2016/054854
§ 371 (c)(1),
(2) Date: Aug. 18, 2017

(87) PCT Pub. No.: WO2016/133197
PCT Pub. Date: Aug. 25, 2016

(65) Prior Publication Data
US 2018/0044402 A1 Feb. 15, 2018

(30) Foreign Application Priority Data

Feb. 20, 2015 (JP) .................... 2015-032231
Dec. 24, 2015 (JP) .................... 2015-252231

(51) Int. Cl.
*A61K 39/00* (2006.01)
*C07K 14/735* (2006.01)

(52) U.S. Cl.
CPC .... *C07K 14/70535* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,565,335 A | 10/1996 | Capon et al. | |
| 2002/0002271 A1 | 1/2002 | Rinderknecht et al. | |
| 2003/0166163 A1 | 9/2003 | Gillies | |
| 2011/0287032 A1 | 11/2011 | Lazar et al. | |
| 2013/0323236 A1 | 12/2013 | Humphreys et al. | |

FOREIGN PATENT DOCUMENTS

| | | | | |
|---|---|---|---|---|
| CN | 101633698 A | 1/2010 | | |
| JP | 2005-511707 A | 4/2005 | | |
| JP | 2006-257098 A | 9/2006 | | |
| JP | 2013-520176 A | 6/2013 | | |
| JP | 2013-538052 A | 10/2013 | | |
| WO | WO 2008/028068 A2 | 3/2008 | | |
| WO | WO 2008/099178 A2 | 8/2008 | | |
| WO | WO 2008/099188 A1 | 8/2008 | | |
| WO | WO-2008099178 A2 * | 8/2008 | ....... C07K 14/70535 |
| WO | WO 2011/056606 A1 | 5/2011 | | |
| WO | WO-2011103584 A2 * | 8/2011 | ....... C07K 14/70521 |
| WO | WO 2012/169735 A2 | 12/2012 | | |
| WO | WO-2012169735 A2 * | 12/2012 | ....... A61K 47/48415 |
| WO | WO 2013/124450 A1 | 8/2013 | | |
| WO | WO 2013/124451 A1 | 8/2013 | | |
| WO | WO 2014/087010 A1 | 6/2014 | | |

OTHER PUBLICATIONS

Haak-Frendscho et al., J Immunol. Jul. 1, 1993;151(1):351-8.*
Google translation of WO 2012/169735, 13 pages, dated Dec. 18, 2017.*
Office Action dated Feb. 21, 2017, in JP 2016-574302.
International Search Report dated May 17, 2016, in PCT/JP2016/054854.
Haak-Frendscho et al., "Human IgE Receptor α-Chain IgG Chimera Blocks Passive Cutaneous Anaphylaxis Reaction In Vivo," The Journal of Immunology, Jul. 1, 1993, 151:351-358.
Supplementary European Search Report dated Jul. 24, 2018, in EP 16752583.1.

* cited by examiner

*Primary Examiner* — Michael Szperka
(74) *Attorney, Agent, or Firm* — Foley & Lardner LLP

(57) ABSTRACT

Provided is an Fc fusion high affinity IgE receptor α-chain having excellent stability at low pH.
An Fc fusion protein comprising:
(i) a high affinity IgE receptor α-chain; and
(ii) an Fc region of IgG1, wherein
a linker fragment region between the (i) and the (ii) is the amino acid sequence shown in SEQ ID NO: 2.

4 Claims, 3 Drawing Sheets

Specification includes a Sequence Listing.

SEQUENCE LISTING

```
<160> NUMBER OF SEQ ID NOS: 4

<210> SEQ ID NO 1
<211> LENGTH: 179
<212> TYPE: PRT
<213> ORGANISM: Homo sapiens

<400> SEQUENCE: 1

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu

<210> SEQ ID NO 2
<211> LENGTH: 14
<212> TYPE: PRT
<213> ORGANISM: Artificial
<220> FEATURE:
```

<223> OTHER INFORMATION: Synthetic

<400> SEQUENCE: 2

Glu Pro Lys Ser Cys Asp Lys Thr His Thr Cys Pro Pro Cys
1               5                   10

<210> SEQ ID NO 3
<211> LENGTH: 411
<212> TYPE: PRT
<213> ORGANISM: Homo sapiens

<400> SEQUENCE: 3

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
        50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
                100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
        130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Glu Pro Lys Ser Cys Asp Lys Thr His Thr Cys Pro Pro
                180                 185                 190

Cys Pro Ala Pro Glu Leu Leu Gly Gly Pro Ser Val Phe Leu Phe Pro
            195                 200                 205

Pro Lys Pro Lys Asp Thr Leu Met Ile Ser Arg Thr Pro Glu Val Thr
        210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
                260                 265                 270

Leu His Gln Asp Trp Leu Asn Gly Lys Glu Tyr Lys Cys Lys Val Ser
            275                 280                 285

Asn Lys Ala Leu Pro Ala Pro Ile Glu Lys Thr Ile Ser Lys Ala Lys
        290                 295                 300

Gly Gln Pro Arg Glu Pro Gln Val Tyr Thr Leu Pro Pro Ser Arg Asp
305                 310                 315                 320

Glu Leu Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu

```
                340             345             350
Asn Asn Tyr Lys Thr Thr Pro Pro Val Leu Asp Ser Asp Gly Ser Phe
        355             360             365

Phe Leu Tyr Ser Lys Leu Thr Val Asp Lys Ser Arg Trp Gln Gln Gly
        370             375             380

Asn Val Phe Ser Cys Ser Val Met His Glu Ala Leu His Asn His Tyr
385             390             395             400

Thr Gln Lys Ser Leu Ser Leu Ser Pro Gly Lys
                405             410

<210> SEQ ID NO 4
<211> LENGTH: 406
<212> TYPE: PRT
<213> ORGANISM: Homo sapiens

<400> SEQUENCE: 4

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
    130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Asp Lys Thr His Thr Cys Pro Pro Cys Pro Ala Pro Glu
            180                 185                 190

Leu Leu Gly Gly Pro Ser Val Phe Leu Phe Pro Pro Lys Pro Lys Asp
        195                 200                 205

Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
            260                 265                 270

Leu Asn Gly Lys Glu Tyr Lys Cys Lys Val Ser Asn Lys Ala Leu Pro
        275                 280                 285

Ala Pro Ile Glu Lys Thr Ile Ser Lys Ala Lys Gly Gln Pro Arg Glu
    290                 295                 300
```

-continued

| | | | | | | | | | | | | |
|---|---|---|---|---|---|---|---|---|---|---|---|---|
| Pro 305 | Gln | Val | Tyr | Thr | Leu 310 | Pro | Pro | Ser | Arg | Asp 315 | Glu | Leu | Thr | Lys | Asn 320 |
| Gln | Val | Ser | Leu | Thr 325 | Cys | Leu | Val | Lys | Gly 330 | Phe | Tyr | Pro | Ser | Asp 335 | Ile |
| Ala | Val | Glu | Trp 340 | Glu | Ser | Asn | Gly | Gln 345 | Pro | Glu | Asn | Asn | Tyr 350 | Lys | Thr |
| Thr | Pro | Pro 355 | Val | Leu | Asp | Ser | Asp 360 | Gly | Ser | Phe | Phe | Leu 365 | Tyr | Ser | Lys |
| Leu | Thr 370 | Val | Asp | Lys | Ser | Arg 375 | Trp | Gln | Gln | Gly | Asn 380 | Val | Phe | Ser | Cys |
| Ser 385 | Val | Met | His | Glu | Ala 390 | Leu | His | Asn | His | Tyr 395 | Thr | Gln | Lys | Ser | Leu 400 |
| Ser | Leu | Ser | Pro | Gly 405 | Lys | | | | | | | | | | |

FC FUSION HIGH AFFINITY IGE RECEPTOR α-CHAIN

CROSS-REFERENCE TO RELATED APPLICATIONS

This application is a National Stage application of PCT/JP2016/054854, filed Feb. 19, 2016, which claims priority from Japanese application nos. JP 2015-032231, filed Feb. 20, 2015, and JP 2015-252231, filed Dec. 24, 2015.

TECHNICAL FIELD

The present invention relates to an Fc fusion high affinity IgE receptor α-chain that is useful as a pharmaceutical product.

More specifically, the present invention relates to an Fc fusion high affinity IgE receptor α-chain having excellent stability at low pH, and a medicinal use thereof.

BACKGROUND ART

Immunoglobulin E(IgE) is one of an immunoglobulin group, which plays a role in allergic reactions. The IgE, which is secreted from B cells or is expressed on the surface of the B cells, binds to a high affinity IgE receptor (FcεRI) found on the surface of mast cells, basophils, etc. When an antigenic protein binds to IgE on a mast cell surface receptor, the IgE becomes a form in which it crosslinks the antigen. Thereafter, chemical mediators such as histamine or serotonin, which are stored in intracellular granules, are released. Consequently, an inflammatory reaction is induced, and type I allergy symptoms such as telangiectasis or vascular hyperpermeability are provoked (Non Patent Literature 1).

Accordingly, since a compound or a protein, which inhibits the binding of IgE to FcεRI, inhibits the binding of the IgE to the FcεRI found on the surface of mast cells, basophils, etc., such a compound or a protein is expected as a therapeutic agent for type I allergic diseases such as bronchial asthma, allergic rhinitis, and allergic conjunctivitis (Non Patent Literature 2).

In recent years, not only a conventional pharmaceutical product comprising, as an active ingredient, a low-molecular-weight compound, but also a protein pharmaceutical product, which strongly binds to a specific receptor or the like in a living body and exhibits excellent therapeutic effects, has been developed. For example, Etanercept has been known as a therapeutic agent for rheumatoid arthritis. Such Etanercept is a completely humanized soluble TNFα/LTα receptor formulation, which has been focused because of the role of a soluble receptor of a tumor necrosis factor (TNF) to suppress the action of TNF in a living body, and has been then developed.

The protein pharmaceutical product can be expected to have high therapeutic effects. On the other hand, it may cause a problem specific to the protein pharmaceutical product in the production process thereof.

In general, when an antibody or an Fc fusion protein is produced in the form of a pharmaceutical product, a purification method of using protein A is applied. In this method, a buffer with a low pH value is used to elute a protein of interest that binds to the protein A. Moreover, in order to inactivate virus, the protein of interest is desirably treated at low pH for a certain period of time.

A protein, which is poor in stability at low pH, easily forms aggregates. If the ratio of aggregates is high, a reduction in purification efficiency or production amount occurs in the production of protein pharmaceutical products. In addition, an immune response is provoked by mixing aggregates into pharmaceutical products, and as a result, serious side effects, such as anaphylaxis, are likely to occur.

As such, the instability of a protein of interest at low pH may be problematic in the production of protein pharmaceutical products.

A polypeptide (immunoadheson) comprising an immunoglobulin and an extracellular domain is disclosed in Patent Literature 1. Patent Literature 1 discloses a high affinity IgE receptor as an example of such immunoadheson. However, this publication does not specifically describe a fused protein of a high affinity IgE receptor and an immunoglobulin.

A fused protein (hereinafter referred to as "Fusion protein A") of a high affinity IgE receptor α-chain (FcεRI α-chain; hereinafter referred to as "FCER1A") and immunoglobulin G1 (IgG1) is disclosed in Non Patent Literature 3. However, the Fusion protein A disclosed in the aforementioned publication is largely different from the protein of the invention of the present application, in terms of the mode of binding FCER1A to IgG1 (Fc). That is to say, the protein of the invention of the present application has a characteristic amino acid sequence in a linker fragment region between the FcεRI and the IgG1.

A fused protein (NPB301) formed by linking a water-soluble fragment of the high affinity IgE receptor (FcεRI) to a human Fc region via a peptide linker is disclosed in Patent Literature 2. However, the protein of the invention of the present application does not comprise the peptide linker disclosed in Patent Literature 2. Moreover, Patent Literature 2 neither discloses nor suggests the characteristic amino acid sequence of the linker fragment region of the present invention.

A fused protein of FCER1A and immunoglobulin G2 (IgG2) is disclosed in Patent Literature 3. However, this fused protein comprising IgG2 is different from the protein of the invention of the present application, in terms of the amino acid sequences of a linker fragment region and an Fc region.

A fused protein of non-human primate FCER1A and IgG1 is disclosed in Patent Literature 4. Moreover, a fused protein of FCER1A and IgG1 is disclosed in Patent Literatures 5 to 7. However, these publications neither disclose nor suggest the characteristic amino acid sequence of the linker fragment region of the present invention.

The aforementioned Non Patent Literature 3 and Patent Literatures 1 to 7 neither disclose nor suggest the protein of the present invention.

CITATION LIST

Patent Literature

Patent Literature 1: U.S. Pat. No. 5,565,335
Patent Literature 2: International Publication WO 2012/169735
Patent Literature 3: Chinese Patent Application Laid-Open No. 101633698
Patent Literature 4: International Publication WO 2008/028068
Patent Literature 5: International Publication WO 2011/056606
Patent Literature 6: International Publication WO 2008/099178

Patent Literature 7: International Publication WO 2008/099188

Non Patent Literature

Non Patent Literature 1: Chisei Ra, "*Allergy no Bunshi Saibo Kiko* (Molecular and Cellular Mechanisms of Allergy)," BIO INDUSTRY, 2008, Vol. 25, No. 9, PP. 23-39
Non Patent Literature 2: Chisei Ra et al., "International Immunology," 1993, Vol. 5, No. 1, PP. 47-54
Non Patent Literature 3: M. Haak-Frendscho et al., "Journal of Immunology," 1993, Vol. 151, No. 1, PP. 351-358

SUMMARY OF INVENTION

Technical Problem

It is an object of the present invention to provide an Fc fusion high affinity IgE receptor α-chain having excellent stability at low pH.

Solution to Problem

The present inventors have conducted intensive studies in order to obtain an Fc fusion high affinity IgE receptor α-chain having high stability against low pH or heat. As a result, the inventors have found that an Fc fusion high affinity IgE receptor α-chain having high stability can be obtained by using a linker fragment comprising three Cys residues, in a fused protein comprising a high affinity IgE receptor α-chain and the Fc region of IgG1, thereby completing the present invention. Specifically, the present invention is as follows.

The present invention relates to the following [1] to [5], etc.

[1] An Fc fusion protein comprising:
  (i) a high affinity IgE receptor α-chain; and
  (ii) an Fc region of IgG1, wherein
  a linker fragment region between the (i) and the (ii) is the amino acid sequence shown in SEQ ID NO: 2.
[2] The Fc fusion protein according to the above [1], comprising the amino acid sequence shown in SEQ ID NO: 3, or an amino acid sequence comprising a deletion of lysine (K) at the C-terminus of the amino acid sequence shown in SEQ ID NO: 3.
[3] The Fc fusion protein according to the above [1] or [2], which is a dimer.
[4] The Fc fusion protein according to the above [3], wherein cysteine residues in the linker fragment region form three disulfide bonds.
[5] A pharmaceutical composition comprising, as an active ingredient, the Fc fusion protein according to any one of the above [1] to [4].

The present description includes the contents as disclosed in Japanese Patent Application No. 2015-032231 and 2015-252231, which are priority documents of the present application.

Advantageous Effects of Invention

The protein of the present invention has excellent stability at low pH. In addition, the protein of the present invention has excellent neutralizing activity against IgE. Accordingly, the protein of the present invention is useful as a protein pharmaceutical product for preventing or treating type I allergic diseases mediated by IgE.

DESCRIPTION OF EMBODIMENTS

Figure 1:
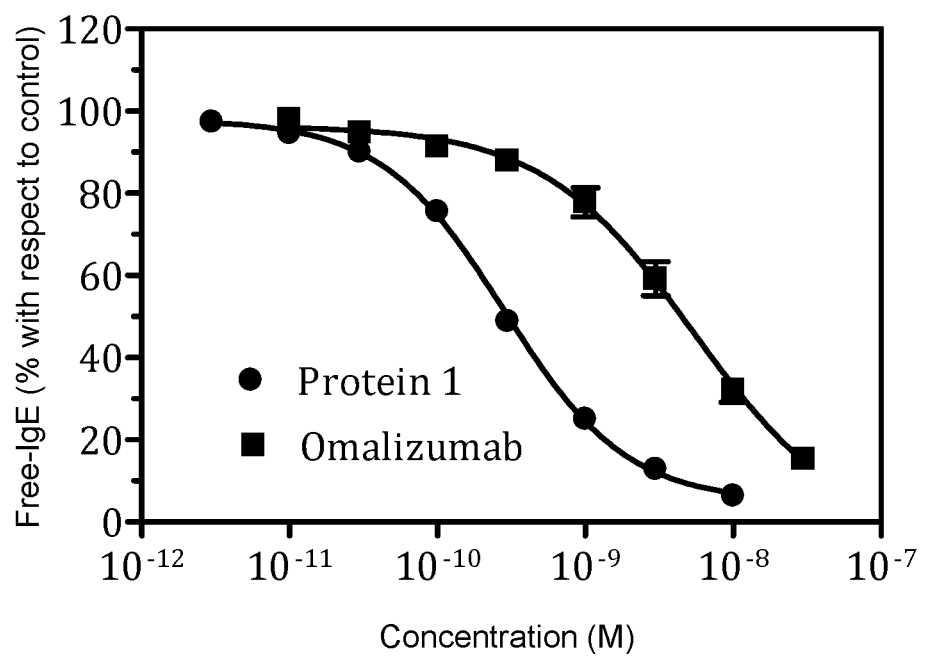
FIG. 1 shows the activity of inhibiting the binding of human IgE. In the figure, the horizontal axis indicates the concentration of each drug (mol/L); and the longitudinal axis indicates the value of the amount of IgE bound to Protein 1 immobilized on a plate, which is shown at a percentage (free IgE (percent with respect to a control)), using, as a reference, the binding amount obtained when a predetermined amount of IgE is added. In the figure, the circle indicates the value of Protein 1, and the square indicates the value of Omalizumab, respectively.

The embodiments of the present invention will be described in detail below.

In the present invention, individual terms have the following meanings, unless otherwise specified.

In the present invention, the "high affinity IgE receptor α-chain (FCER1A)" means a protein comprising an α-chain portion that is an extracellular domain of a high affinity IgE receptor. The high affinity IgE receptor α-chain is, for example, a protein shown in the following SEQ ID NO: 1.

SEQ ID NO: 1:
VPQKPKVSLNPPWNRIFKGENVTLTCNGNNFFEVSSTKWFHNGSLSEETN

SSLNIVNAKFEDSGEYKCQHQQVNESEPVYLEVFSDWLLLQASAEVVMEG

QPLFLRCHGWRNWDVYKVIYYKDGEALKYWYENHNISITNATVEDSGTYY

CTGKVWQLDYESEPLNITVIKAPREKYWL

The above-described high affinity IgE receptor α-chain includes, for example, a protein having identity of 90% or more, 95% or more, 97% or more, or 99% or more to the amino acid sequence shown in SEQ ID NO: 1, when the identity is calculated using BLAST (Basic Local Alignment Search Tool at the National Center for Biological Information) or the like (e.g., using default parameters), and having binding ability to IgE. Moreover, the high affinity IgE receptor α-chain also includes a protein comprising an amino acid sequence having a substitution, deletion and/or addition of one or more, or several amino acids (1 to 10, preferably 1 to 5, and more preferably 1 or 2 amino acids) with respect to the amino acid sequence shown in SEQ ID NO: 1, and having binding ability to IgE.

In the present invention, the "Fc region of IgG1" means the Fc fragment of immunoglobulin G1, namely, the CH2 and CH3 constant domains of native immunoglobulin G1.

The Fc region of IgG1 includes all of a natural mutant, an artificial mutant, and a truncated form.

In the present invention, the "linker fragment region between the high affinity IgE receptor α-chain and the Fc region of IgG1" means a region consisting of 14 amino acid residues ranging from the junction point between the above-described high affinity IgE receptor α-chain and the above described Fc region of IgG1 towards the direction of the Fc region.

In the present invention, the "Fc fusion protein" means a recombinant protein comprising the high affinity IgE receptor α-chain and the Fc fragment of an immunoglobulin.

The protein of the present invention is characterized in that the linker fragment region between the high affinity IgE receptor α-chain and the Fc region of IgG1 is the amino acid sequence shown in the following SEQ ID NO: 2.

```
SEQ ID NO: 2:
EPKSCDKTHTCPPC
```

The protein of the present invention is preferably an Fc fusion protein comprising the amino acid sequence shown in the following SEQ ID NO: 3 (hereinafter referred to as "Protein 1").

```
SEQ ID NO: 3:
VPQKPKVSLNPPWNRIFKGENVTLTCNGNNFFEVSSTKWFHNGSLSEET

NSSLNIVNAKFEDSGEYKCQHQQVNESEPVYLEVFSDWLLLQASAEVVM

EGQPLFLRCHGWRNWDVYKVIYYKDGEALKYWYENHNISITNATVEDSG

TYYCTGKVWQLDYESEPLNITVIKAPREKYWLEPKSCDKTHTCPPCPAP

ELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVM

HEALHNHYTQKSLSLSPGK
```

The amino acid sequence shown in SEQ ID NO: 3 has a sequence formed by fusing the amino acid sequence shown in SEQ ID NO: 1 (from Val at position 1 to Leu at position 179 of the amino acid sequence shown in SEQ ID NO: 3), the amino acid sequence shown in SEQ ID NO: 2 (Glu at position 180 to Cys at position 193 of the amino acid sequence shown in SEQ ID NO: 3), and the amino acid sequence of the Fc fragment of an immunoglobulin (Pro at position 194 to Lys 411 of the amino acid sequence shown in SEQ ID NO: 3) in this order. This Fc fusion protein includes a protein comprising an amino acid sequence having identity of 90% or more, 95% or more, 97% or more, or 99% or more to the amino acid sequence shown in SEQ ID NO: 3, which is other than the amino acid sequence portion from Glu at position 180 to Cys at position 193 that corresponds to the amino acid sequence shown in SEQ ID NO: 2, when the identity is calculated using, for example, BLAST (Basic Local Alignment Search Tool at the National Center for Biological Information) or the like (e.g., using default parameters), and having binding ability to IgE. Moreover, this Fc fusion protein includes a protein comprising an amino acid sequence having a substitution, deletion and/or addition of one or more, or several amino acids (1 to 10, preferably 1 to 5, and more preferably 1 or 2 amino acids) with respect to the amino acid sequence shown in SEQ ID NO: 3, which is other than the amino acid sequence portion from Glu at position 180 to Cys at position 193 that corresponds to the amino acid sequence shown in SEQ ID NO: 2, and having binding ability to IgE.

Upon the production of a recombinant antibody, there is a case where the lysine at the C-terminus is deleted by post-translational modification. Accordingly, the protein of the present invention may be an Fc fusion protein comprising an amino acid sequence having a deletion of the lysine (K) at the C-terminus of the above-described Protein 1. For example, such an Fc fusion protein comprising an amino acid sequence having a deletion of the lysine (K) at the C-terminus of Protein 1 shown in SEQ ID NO: 3 consists of an amino acid sequence portion from the position 1 to the position 410 of the amino acid sequence shown in SEQ ID NO: 3.

The protein of the present invention includes both a monomer and a dimer of an Fc fusion protein formed by linking a high affinity IgE receptor α-chain to the Fc region of IgG1 via a linker fragment consisting of the amino acid sequence shown in SEQ ID NO: 2. Three Cys residues are present in the above-described linker fragment region (the Cys residues at positions 184, 190, and 193 of the amino acid sequence shown in SEQ ID NO: 3), and a dimer can be formed by disulfide bonds. In general, two Fc fusion protein monomers form a dimer as a result of the formation of three disulfide bonds between Cys residues at the same positions as those of the above-described three Cys residues, and the above-described three Cys residues. Because of the above-described three disulfide bonds, a dimer is stabilized, and it has high stability against low pH and heat. The phrase "having high stability against low pH and heat" means, for example, that only a few aggregates are formed under conditions of low pH and under heating. Such high stability against low pH or heat can be confirmed, for example, by performing a low pH treatment or a heat treatment on a protein, and then measuring the content of aggregates in the protein by gel filtration chromatography. For example, even if the Fc fusion protein of the present invention is preserved at a low temperature of 2° C. to 8° C., and preferably 4° C., at pH 1 to 5, and preferably at pH 2 to 4, for 1 day to 1 month, preferably for 1 day to 14 days, and more preferably for 5 to 12 days, or even if the present Fc fusion protein is preserved at a temperature of 25° C. to 45° C., and preferably 30° C. to 40° C., for 1 day to 1 month, preferably 1 day to 14 days, and more preferably 1 day to 7 days, a change in the content rate of aggregates is small. For example, when a change in the content rate of aggregates in the protein of the present invention is calculated based on the peak area of gel filtration chromatography, it is 10% or less, and preferably 8% or less. Further, when compared with an Fc fusion protein having two or less Cys residues as a linker fragment, a change in the content rate of aggregates in the protein of the present invention is small.

The protein of the present invention can be produced, for example, by the following method or a method equivalent thereto, or by the methods described in publications or methods equivalent thereto.

The protein of the present invention can be produced using a genetic recombination technique that is well known to a person skilled in the present technical field. For example, DNA encoding the protein of the present invention is prepared, and an expression vector comprising this DNA is then constructed. Subsequently, prokaryotic or eukaryotic cells are transformed or transfected with the above-described vector, and a protein of interest can be isolated and purified from a culture supernatant of the obtained cells.

The protein of the present invention can also be produced using protein-expressing cells that are well known to a person skilled in the present technical field. For example, cDNA encoding the amino acid sequence shown in SEQ ID NO: 3 is incorporated into a mammalian expression plasmid vector to prepare a protein expression plasmid, and the prepared plasmid is then introduced into animal cells such as Chinese hamster ovary cells (CHO), so as to establish a stable expression cell line. The obtained cells are cultured, and then, the protein of the present invention can be obtained from a culture supernatant.

The protein of the present invention can be isolated and purified, as necessary, by isolation and purification means that are well known to a person skilled in the present technical field. Examples of the isolation and purification method include affinity chromatography, ion exchange chromatography, gel filtration chromatography, hydrophobic chromatography, mixed mode chromatography, dialysis, a fractional precipitation method, and electrophoresis. The protein of the present invention can also be isolated and purified by combining these methods with one another, as appropriate.

The protein of the present invention may also undergo chemical modification that is well known to a person skilled in the present technical field. Examples of the chemical modification include glycosylation, polyethylene glycolation (PEG), acetylation, and amidation.

Since the protein of the present invention has neutralizing activity against IgE, it can be used as a preventive or therapeutic agent for various diseases mediated by IgE. For instance, the protein of the invention of the present application is useful as a preventive or therapeutic agent for diseases associated with type I allergy, and the like, such as bronchial asthma, eosinophilic otitis media, eosinophilic sinusitis, allergic conjunctivitis, allergic rhinitis, pollinosis, food allergy, mite allergic disease, hives, and anaphylactic shock.

The protein of the present invention has excellent affinity for IgE. Hence, the protein of the present invention can also be used as a "protein-drug conjugate" that utilizes such affinity, such as an antibody-drug conjugate (ADC). Examples of such a "protein-drug conjugate" include the modes of use, such as "Protein 1-drug" and "Protein 1-linker-drug." As a drug, an anti-allergic agent or the like can be used. Such a conjugate can be produced by a method well known to a person skilled in the present technical field.

With regard to the pharmaceutical composition of the present invention, various dosage forms are used depending on usage. Examples of an oral agent include a tablet, a powder agent, a granule, a fine granule, and a capsule. Examples of a parenteral agent include an injection, inhalation powders, an inhalation liquid, eye drops, a liquid agent, a lotion agent, a spray agent, nasal drops, a drip, an ointment, a suppository, and a patch.

The pharmaceutical composition of the present invention is administered by various administration methods, depending on usage. Examples of the administration method include oral administration, intravenous administration, intraperitoneal administration, subcutaneous administration, topical administration, and intramuscular administration.

The pharmaceutical composition of the present invention is prepared using the protein of the present invention and at least one pharmaceutical product additive. The pharmaceutical composition of the present invention can be prepared by a known pharmaceutical method, depending on its dosage form. Examples of such a pharmaceutical product additive include an excipient, a disintegrator, a binder, a lubricant, a diluent, a buffer, a tonicity agent, a preservative, a stabilizer, and a solubilizer. The above-described pharmaceutical product additive also includes a physiological saline and water for injection. The pharmaceutical composition of the present invention can be prepared by being mixed with, being diluted with, or being dissolved in the above-described pharmaceutical product additives.

When the pharmaceutical composition of the present invention is used for prevention or treatment, the dose of the protein of the present invention, which is comprised therein as an active ingredient, is determined, as appropriate, depending on the age, sex, and body weight of a patient, the degree of disease, a dosage form, an administration route, etc. With regard to the dose applied to an adult by oral administration, the applied dose can be determined, for example, in the range of 0.1 µg/kg to 1000 mg/kg/day. The daily dose in the case of oral administration is preferably in the range of 0.1 mg/kg to 10 mg/kg/day, depending on the dosage form. Such a daily dose may be administered at once, or dividedly over two or three administrations. Moreover, the dose applied to an adult by parenteral administration can be determined in the range of 0.01 µg/kg to 1000 mg/kg/day. The daily dose in the case of parenteral administration is in the range of preferably 0.1 µg/kg to 10 µg/kg/day, 1 µg/kg to 100 µg/kg/day, or 10 µg/kg to 1000 µg/kg/day, depending on the dosage form.

EXAMPLES

The content of the present invention will be described in more detail in the following examples and test examples. However, these examples are not intended to limit the scope of the present invention.

Example 1

Expression and Preparation of Protein 1
(1) Preparation of Protein 1 Expression Vector
cDNA encoding the amino acid sequence shown in SEQ ID NO: 3 was incorporated into a mammalian expression plasmid vector to prepare a Protein 1 expression plasmid.
(2) Preparation of Protein 1-Expressing Cells
The Protein 1 expression plasmid was introduced into Chinese hamster ovary cells (CHO) to establish a Protein 1 stable expression cell line. Secretion of Protein 1 into a culture supernatant was confirmed by SDS-PAGE.

Test Example 1

IgE Binding Inhibitory Activity (IgE Neutralizing Activity)
(1) Preparation of Assay Plate
Protein 1 was dissolved in a coating buffer, and an aliquot of the obtained solution was added onto a microplate. The microplate was left at 4° C. for 18 or more hours, and was then washed with a washing buffer (PBS-Tween 20). Thereafter, a blocking solution (Assay Diluent) (BD Biosciences) was added thereto. The microplate was left at room temperature for 1 hour, and the blocking solution was then removed. The plate was washed with a washing buffer, and was then used in the measurement of binding inhibitory activity.
(2) Method of Measuring Binding Inhibitory Activity
Using omalizumab (anti-human IgE antibody) as a positive control, the IgE binding inhibitory activity of Protein 1 was measured by the following method.
A certain amount of human IgE (ANTIBODYSHOP) was mixed with Protein 1 or omalizumab (Novartis) having any given concentration. The obtained mixture was added to the plate prepared in the above (1), and it was then left at room temperature for approximately 2 hours. After the mixed solution had been discarded, the plate was washed with a washing buffer. A HRP-labeled anti-human IgE antibody (BD Biosciences) was added to the resulting plate, and it was then left at room temperature for approximately 1 hour. After the antibody solution had been discarded, the plate was washed with a washing buffer. A TMB (3,3',5,5'-tetramethylbenzidine) solution was added to the plate. After a certain period of time had passed, phosphoric acid was added to the plate to terminate a coloring reaction. Thereafter, using a plate reader, absorbance (OD450) was measured. Based on the amount of IgE bound to Protein 1 immobilized on the plate, Protein 1 and omalizumab were evaluated in terms of IgE binding inhibitory activity (IgE neutralizing activity) (FIG. 1).

(3) Results

The Protein 1 of the present invention inhibited the binding of IgE to FCER1A in a concentration-dependent manner.

Test Example 2

Test Regarding Stability at Low pH
(1) Preparation of Sample

A purification operation was carried out using AKTA Explorer 10 S (GE Healthcare). Protein 1 was allowed to be expressed by the same method as that described in Example 1, and then, a culture supernatant thereof was 2 times diluted with D-PBS(-) (Dulbecco's Phosphate Buffered Saline). The diluted solution was loaded on HiTrap rProtein A FF (GE Healthcare, 17-5079-01). The above-described column was washed with D-PBS(-), and was then eluted with a 100 mM glycine-HCl buffer (pH 2.2). A protein A adsorption fraction was fractionated at 1.0 mL/tube. The peak fractions were mixed with one another to obtain a low pH-treated sample (pH 2.9). The low pH-treated sample that had been preserved at 4° C. was used as an evaluation sample. 0.25 mL of an aliquot was sampled from the evaluation sample at a predetermined timing (5 to 12 days after the preservation at 4° C.), and 0.05 mL of a 1 M Tris-HCl buffer (pH 9.0) was added to the aliquot to neutralize it, thereby obtaining a neutralized sample.

As a control, Fusion protein A described in Non Patent Literature 3 was used. Fusion protein A was allowed to be expressed by the same method as that described in Example 1, and then, a neutralized sample was obtained by the same method as the aforementioned method. It is to be noted that the Fusion protein A used in the present test is a protein consisting of the amino acid sequence shown in the following SEQ ID NO: 4. The amino acid sequence shown in SEQ ID NO: 4 comprises a linker fragment consisting of Asp at position 180 to Cys at position 188, and the number of Cys residues contained in this linker fragment is 2.

SEQ ID NO: 4:
VPQKPKVSLNPPWNRIFKGENVTLTCNGNNFFEVSSTKWFHNGSLSEET

NSSLNIVNAKFEDSGEYKCQHQQVNESEPVYLEVFSDWLLLQASAEVVM

EGQPLFLRCHGWRNWDVYKVIYYKDGEALKYWYENHNISITNATVEDSG

TYYCTGKVWQLDYESEPLNITVIKAPREKYWLDKTHTCPPCPAPELLGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALH

NHYTQKSLSLSPGK (2) Method of Analyzing Content of Aggregates

Figure 2:
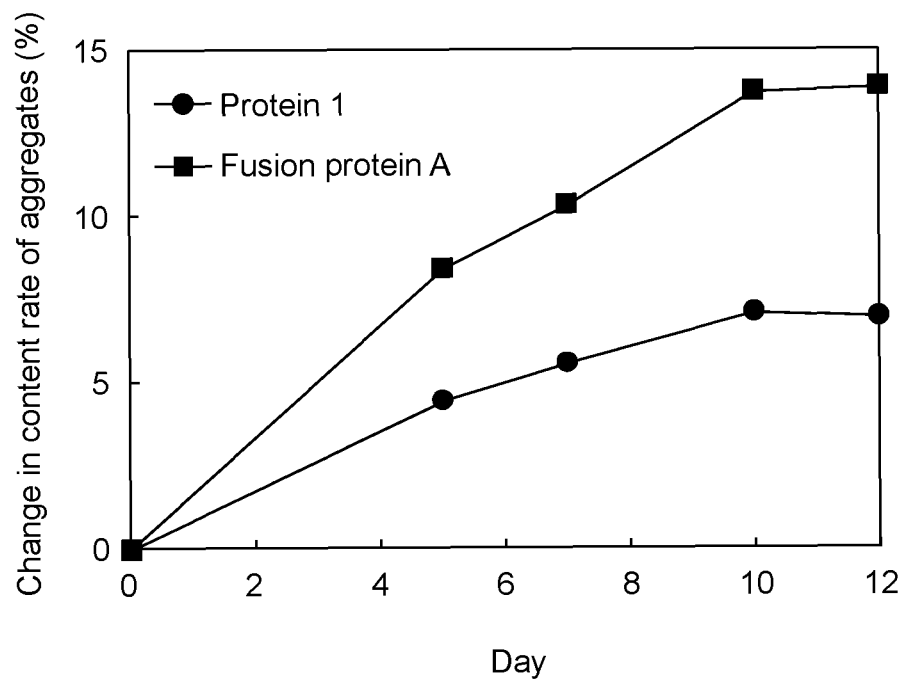
FIG. 2 shows a transition of a change in the content rate (%) of aggregates at low pH. In the figure, the horizontal axis indicates the number of days (Day), and the longitudinal axis indicates a change in the content rate (%) of aggregates. In the figure, the circle indicates the value of Protein 1, and the square indicates the value of Fusion protein A, respectively.

With regard to the operation of analyzing aggregates, the content of aggregates was confirmed by performing gel filtration chromatography of using Superdex 200 10/300GL (GE Healthcare, 17-5175-01), employing AKTA Explorer 10 S (GE Healthcare), and also using D-PBS(-) as a mobile phase. The areas of a peak whose eluted position was a monomer and an aggregate peak eluted in a high molecular region were calculated, and a transition of a change in the content rate of aggregates (%) in Protein 1 and Fusion protein A, which was caused by a low pH treatment, was evaluated (FIG. 2).

(3) Results

In the protein of the present invention, the increased level of the formation of aggregates associated with a low pH treatment time was significantly smaller than that in the case of Fusion protein A, and thus, the protein of the present invention exhibited high stability against exposure to low pH. Therefore, the protein of the present invention is excellent in terms of stability at low pH, and thus, the improvement of purification efficiency and productivity is expected in the production process.

Test Example 3

Test Regarding Stability Against Heat
(1) Preparation of Sample

A purification operation was carried out using AKTA Explorer 10 S (GE Healthcare). Protein 1 was allowed to be expressed by the same method as that described in Example 1, and a culture supernatant thereof was then loaded on HiTrap MabSelect SuRe (GE Healthcare, 17-0034-94). The above-described column was washed with D-PBS(-) and a 100 mM citrate buffer (pH 4.0), and a protein A adsorbate was then eluted with a 100 mM glycine-HCl buffer (pH 3.3). A 1 M Tris-HCl buffer (pH 9.0) was added at a volume of 1/10 to the recovered fraction to neutralize it, so as to obtain a protein A-purified protein. The pH of this protein A-purified protein was adjusted to pH 4.0 by addition of 1 N HCl, and it was then loaded on a column filled with a mixed mode resin of hydrophobic interaction and cation exchange. A non-adsorbed protein was washed with a 50 mM acetate buffer (pH 4.0), and 100% linear gradient elution was then carried out with a 50 mM Tris-Hcl buffer (pH 9.0). A peak fraction was recovered to obtain a purified protein. The obtained protein was subjected to gel filtration fractionation, using D-PBS(-) as a mobile phase, and employing HiLoad 16/60 Superdex 200 prep grade (GE Healthcare, 17-1069-01). A peak fraction corresponding to a monomer was recovered to obtain a gel filtration purified sample. This gel filtration purified sample was adjusted again with D-PBS(-), and it was then poured into a microtube, followed by incubation at 37° C., so as to obtain an evaluation sample. An aliquot was sampled from this evaluation sample at a predetermined timing (1 day to 7 days after the preservation at 37° C.), so as to obtain a heat treatment sample.

As a control, Fusion protein A described in Non Patent Literature 3 was used. Fusion protein A was allowed to be expressed by the same method as that in Example 1, and then, a heat treatment sample was obtained by the same method as the aforementioned method. It is to be noted that the Fusion protein A used in the present test is a protein consisting of the same amino acid sequence as that of the protein used in Test Example 2.

(2) Method of Analyzing Content of Aggregates

Figure 3:
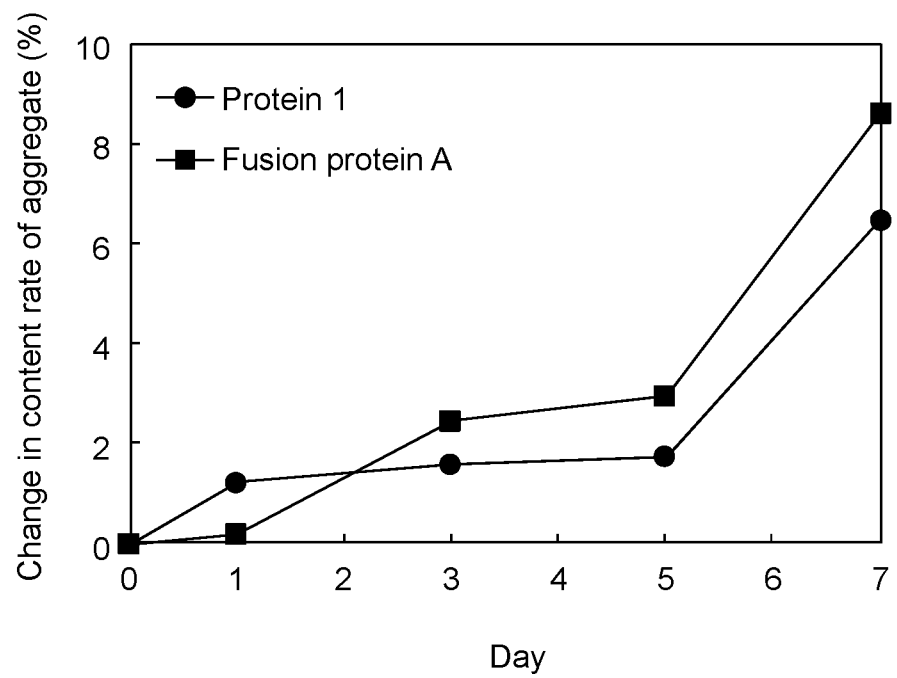
FIG. 3 shows a transition of a change in the content rate (%) of aggregates by a heat treatment. In the figure, the horizontal axis indicates the number of days (Day), and the longitudinal axis indicates a change in the content rate (%) of aggregates. In the figure, the circle indicates the value of Protein 1, and the square indicates the value of Fusion protein A, respectively.

With regard to the operation of analyzing aggregates, the content of aggregates was confirmed by performing gel filtration chromatography of using Superdex 200 10/300GL (GE Healthcare, 17-5175-01), employing AKTA Explorer 10 S (GE Healthcare), and also using D-PBS(−) as a mobile phase. The areas of a peak whose eluted position was a monomer and an aggregate peak eluted in a high molecular region were calculated, and a transition of a change in the content rate of aggregates (%) in Protein 1 and Fusion protein A, which was caused by a heat treatment, was evaluated (FIG. 3).

(3) Results

In the protein of the present invention, the increased level of the content of aggregates after preservation at 37° C. was smaller than that in the case of Fusion protein A, and thus, the protein of the present invention exhibited more stability against exposure at 37° C. Therefore, the protein of the present invention is excellent in terms of stability against heat, as well as stability at low pH, and thus, the improvement of purification efficiency and productivity is expected in the production process.

INDUSTRIAL APPLICABILITY

Since the protein of the present invention has excellent neutralizing activity against IgE, it can be used as a protein pharmaceutical product for preventing or treating various diseases mediated by the IgE.

Sequencing Free Text

SEQ ID NO: 2 Synthesized

All publications, patents and patent applications cited in the present description are incorporated herein by reference in their entirety.

The invention claimed is:

1. An Fc fusion protein comprising:
   (i) a high affinity IgE receptor α-chain;
   (ii) an Fc region of IgG1; and
   (iii) the amino acid sequence shown in SEQ ID NO: 3, or an amino acid sequence comprising a deletion of lysine (K) at the C-terminus of the amino acid sequence shown in SEQ ID NO: 3, wherein
   a linker fragment region between (i) and (ii) is the amino acid sequence shown in SEQ ID NO: 2.

2. The Fc fusion protein according to claim 1, which is a dimer.

3. The Fc fusion protein according to claim 2, wherein cysteine residues in the linker fragment region form three disulfide bonds.

4. A pharmaceutical composition comprising, as an active ingredient, the Fc fusion protein according to claim 1.

* * * * *